(12) United States Patent
Cincotta

(10) Patent No.: US 8,137,994 B2
(45) Date of Patent: *Mar. 20, 2012

(54) METHODS OF IDENTIFYING RESPONDERS TO DOPAMINE AGONIST THERAPY AND TREATING METABOLIC CONDITIONS THEREOF

(75) Inventor: Anthony H. Cincotta, Tiverton, RI (US)

(73) Assignee: VeroScience LLC, Tiverton, RI (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/066,280

(22) Filed: Apr. 11, 2011

(65) Prior Publication Data

US 2011/0195971 A1    Aug. 11, 2011

Related U.S. Application Data

(63) Continuation-in-part of application No. 12/931,859, filed on Feb. 11, 2011, which is a continuation of application No. 12/322,319, filed on Jan. 30, 2009, now Pat. No. 7,888,310, which is a continuation of application No. 11/086,937, filed on Mar. 22, 2005, now abandoned.

(60) Provisional application No. 60/556,309, filed on Mar. 25, 2004.

(51) Int. Cl.
| | |
|---|---|
| *G01N 33/53* | (2006.01) |
| *C12Q 1/00* | (2006.01) |
| *A01N 61/00* | (2006.01) |
| *A01N 43/58* | (2006.01) |
| *A01N 43/60* | (2006.01) |
| *A61K 31/00* | (2006.01) |
| *A61K 31/50* | (2006.01) |
| *A61K 31/495* | (2006.01) |
| *G01J 3/42* | (2006.01) |
| *G01J 3/427* | (2006.01) |
| *G01N 13/00* | (2006.01) |
| *G01N 30/84* | (2006.01) |

(52) U.S. Cl. ............... 436/815; 435/4; 514/1; 514/250; 356/319; 73/61.55

(58) Field of Classification Search ................. None
See application file for complete search history.

(56) References Cited

U.S. PATENT DOCUMENTS

| | | |
|---|---|---|
| 5,741,503 A | 4/1998 | Cincotta et al. |
| 5,877,183 A | 3/1999 | Cincotta |
| 6,040,292 A | 3/2000 | Sommer |
| 6,166,017 A | 12/2000 | Marin |
| 6,197,765 B1 | 3/2001 | Vardi et al. |
| 6,322,976 B1 | 11/2001 | Altman et al. |
| 6,376,464 B1 | 4/2002 | Dasseux et al. |
| 6,410,339 B1 | 6/2002 | Marin |
| 6,441,036 B1 | 8/2002 | Berge |
| 6,506,799 B1 | 1/2003 | Dasseux |

*Primary Examiner* — Robert Landsman
(74) *Attorney, Agent, or Firm* — Todd E. Garabedian; Wiggin and Dana LLP

(57) ABSTRACT

The present invention is directed to a method of identifying patients to be treated by dopamine agonist therapy comprising the step of analyzing a plasma or urine sample from said patient for concentrations of norepinephrine (NE), norepinephrine metabolites (NE metabolites), dopamine, dopamine metabolites, serotonin, serotonin metabolites, or fasting triglycerides, wherein one or more of: (a) NE metabolites, (b) NE/NE metabolites: dopamine/dopamine metabolites, (c) NE and serotonin, (d) NE/NE metabolites and serotonin, (e) NE and serotonin metabolites, (f) NE/NE metabolites and serotonin metabolites, or (g) NE is/are greater than about 30% over normal level; or dopamine/dopamine metabolites are less than about 30% below normal; or said patient has hypertriglyceridemai and/or hypertension. The present invention is also directed to treating identified patients with dopamine agonist therapy.

4 Claims, No Drawings

METHODS OF IDENTIFYING RESPONDERS TO DOPAMINE AGONIST THERAPY AND TREATING METABOLIC CONDITIONS THEREOF

CROSS-REFERENCE TO RELATED APPLICATIONS

This application is a Continuation-in-Part of U.S. Ser. No. 12/931,859 filed Feb. 11, 2011, which is a Continuation of U.S. Ser. No. 12/322,319 filed Jan. 30, 2009, now U.S. Pat. No. 7,888,310, which is a Continuation application of U.S. Ser. No. 11/086,937 filed Mar. 22, 2005, abandoned, which claims the benefit of U.S. Provisional Application Ser. No. 60/556,309 filed Mar. 25, 2004.

BACKGROUND OF THE INVENTION

1. Field of the Invention

This invention relates to a method for identifying individuals suffering from metabolic disorders such as diabetes, pre-diabetes, Metabolic Syndrome, or obesity, who will respond to dopamine agonist therapy. More particularly, this invention relates to testing bodily fluids such as plasma or urine samples of individuals suffering from the above disorders to determine if those individuals will respond favorably to dopamine agonist therapy.

2. Description of the Related Art

Metabolism is a complex orchestration of biochemical processes among cells and tissues of the body all working in concert to ensure the survival of the organism as a whole. The central nervous system plays a major role in integrating these metabolic activities to maintain normal biological homeostasis within the body. Environmental and genetic perturbations to this central nervous system control of metabolism can manifest as a range of metabolic disorders. Additionally, since metabolic processes have profound effects on the entire body, diseases and disorders affecting metabolism generally affect other areas of the body as well. For example, individuals suffering from Type 2 diabetes often experience problems with other body organs and systems. Typically, plasma glucose levels are elevated in Type 2 diabetes as a result of the body's resistance to the glucose-lowering effects of a hormone called insulin. Type 2 diabetes is associated with damage to various organs such as the eyes, nerves, and kidneys. The disease is also associated with substantially increased risk for cardiovascular disease, the leading cause of death in Type 2 diabetics. The prevalence of Type 2 diabetes is reaching epidemic proportions in the United States and around the world.

To be diagnosed with Type 2 diabetes, an individual must have a fasting plasma glucose level greater than or equal to 126 mg/dl or a 2-hour oral glucose tolerance test (OGTT) plasma glucose value of greater than or equal to 200 mg/dl (*Diabetes Care* 26: S5-S20, 2003). A related condition called pre-diabetes is defined as having a fasting glucose level of greater than 100 mg/dl but less than 126 mg/dl or a 2-hour OGTT plasma glucose level of greater than 140 mg/dl but less than 200 mg/dl. Mounting evidence suggests that the pre-diabetes condition may be a risk factor for developing cardiovascular disease (*Diabetes Care* 26: 2910-2914, 2003).

Metabolic Syndrome, also referred to as Syndrome X, is another metabolic disorder that affects other pathways and systems in the body. Originally, Metabolic Syndrome was defined as a cluster of metabolic disorders (including obesity, insulin resistance, hypertension, and dyslipidemia primarily hypertriglyceridemia), that synergize to potentiate cardiovascular disease. As defined herein, hypertension is defined as a systolic blood pressure of greater than or equal to 140 mmHg or a diastolic blood pressure of greater than or equal to 90 mmHg, and/or current use of antihypertensive medication (see: Seventh Report of the Joint National Committee on Prevention, Detection, Evaluation, and Treatment of High Blood Pressure (2003)). More recently, the U.S. National Cholesterol Education Program has classified Metabolic Syndrome as meeting three out of the following five criteria: fasting glucose level of at least 110 mg/dl, plasma triglyceride level of at least 150 mg/dl (hypertriglycerdemia), HDL cholesterol below 40 mg/dl in men or below 50 mg/dl in women, blood pressure at least 130/85 mm Hg, and central obesity, with central obesity being defined as abdominal waist circumference greater than 40 inches for men and greater than 35 inches for women. The American Diabetes Association estimates that 1 in every 5 overweight people suffer from Metabolic Syndrome.

While these disorders and diseases are related, it is clear that they have individual and distinct pathologies. For that reason, drugs used to treat one disorder may not be effective against another disorder. For instance, drugs that are effective in treating Type 2 diabetes or pre-diabetes have little to no effect on Metabolic Syndrome. Additionally, certain drugs used to treat Type 2 diabetes or pre-diabetes may increase blood pressure (hypertension) or cause weight gain in the individuals taking the medication. For example, thiazolidinediones used in the treatment of Type 2 diabetes causes weight gain and have marginal effects on hypertension. Another anti-diabetic agent, metformin, also has marginal effects on hypertension and hypertriglyceridemia. Insulin, which is a hormone used to treat Type 2 diabetes, can potentiate hypertension and weight gain. Individuals suffering from metabolic disorders carry an increased risk of cardiovascular disease as a result of their hypertension and obesity. Therefore, side effects such as hypertension and weight gain have damaging effects on those individuals. Consequently, those individuals cannot take commonly prescribed medication to control their metabolic disorders.

Dopamine agonist therapy has been effective in reducing hyperglycemia, glucose intolerance, hyperinsulinemia, insulin resistance, and/or plasma lipid levels in mammals, including humans. Dopamine agonist therapy has also been found to be an effective therapy for some individuals suffering from metabolic disorders. However, not all individuals respond well to these therapies. For example, treatment of Type 2 diabetics with bromocriptine, a dopamine agonist, produces a bimodal distribution of responses in terms of improving glycemic control over a 24 week treatment period when "responders" are defined as those individuals that reduce percent glycosylated hemoglobin Alc (HbAlc) level by 0.3 within an 8 week period from the initiation of dopamine agonist treatment. The average percent HbAlc reduction among such responders was −0.63 and this group represented 65% of the total treated population. Among the remaining 35% of the treated population (non-responders), the average percent HbAlc change was approximately +0.4 (*Exp. Opin. Invest. Drugs* 8:1683-1707, 1999). Clearly, using this criteria, there is a bimodal distribution of responses to dopamine agonist therapy among these Type 2 diabetic individuals.

As with all medical therapies, it is a goal to minimize exposure to unnecessary or inappropriate treatment, as well as reduce or eliminate the risk of unwanted side effects. It has been found that dopamine agonist therapy reduces or eliminates unwanted side effects that other medications for the treatment of a metabolic disorder may cause. The treatment would be more beneficial if there was a method to identify individuals who would respond to the dopamine agonist therapy.

A variety of treatments are available for diseases associated with obesity, including Type 2 Diabetes. For example, U.S. Pat. No. 6,506,799 discloses methods of treating cardiovascular diseases, dyslipidemia, dyslipoproteinemia, and hypertension comprising administering a composition comprising an ether compound.

U.S. Pat. No. 6,441,036 discloses fatty acid analogous which can be used for the treatment and/or prevention of obesity, fatty liver and hypertension.

U.S. Pat. No. 6,410,339 discloses use of cortisol agonist for preparing a system for diagnosis of the Metabolic Syndrome and related conditions as belly fatness, insulin resistance including increased risk of developing senile diabetes, i.e., diabetes type II, high blood fats and high blood pressure, in which system the dose of cortisol agonist is in an interval where a difference is obtained in the inhibitory effect of the autoproduction of cortisol in individuals suffering from the Metabolic Syndrome, compared to normal values.

U.S. Pat. No. 6,376,464 discloses peptides and peptide analogues that mimic the structural and pharmacological properties of human ApoA-I. The peptides and peptide analogues are useful to treat a variety of disorders associated with dyslipidemia.

U.S. Pat. No. 6,322,976 discloses, among other things, methods of diagnosing a disease associated with a defect in insulin action, glucose metabolism, fatty acid metabolism, and/or catecholamine action by detecting a mutation in the CD36 gene.

U.S. Pat. No. 6,197,765 discloses a treatment for Metabolic Syndrome (syndrome-X), and resulting complications, by administration of diazoxide.

U.S. Pat. No. 6,166,017 discloses a method for the medical treatment of diabetes mellitus type II and for counteracting the risk factors forming part of the Metabolic Syndrome by administration of ketoconazole.

U.S. Pat. No. 6,040,292 discloses methods for the treatment of diabetes mellitus, including type I, type II, and insulin resistant diabetes (both type I and type II). The methods of the invention employ administration of rhIGF-I/IGFBP-3 complex to a subject suffering from the symptoms of diabetes mellitus. Administration of rhIGF-UIGFBP-3 to a subject suffering from the symptoms of diabetes mellitus results in amelioration or stabilization of the symptoms of diabetes.

U.S. Pat. No. 5,877,183 discloses methods for the regulation and modification of lipid and glucose metabolism, but not Metabolic Syndrome, by administering to a subject a dopamine D1 agonist, optionally in combination with a dopamine D2 agonist, an alpha-1 adrenergic antagonist, an alpha-2 adrenergic agonist, or a serotonergic inhibitor, or optionally in combination with a dopamine D2 agonist coadministered with at least one of alpha-1 adrenergic antagonist, an alpha-2 adrenergic agonist, or a serotonergic inhibitor, and further administering the subject a serotonin $5HT_{1b}$ agonist. It is well known that dopamine agonists function to both activate and deactivate dopamine receptors and thereby reduce dopaminergic neuronal activity.

U.S. Pat. No. 5,741,503 discloses methods for regulating or ameliorating lipid metabolism which comprise administration or timed administration of inhibitors of dopamine beta hydroxylase (DBH). However, the focus of this technology is reduction in noradrenergic neuronal activity level only and does not increase dopaminergic neuronal activity inasmuch as DBH is not present in dopaminergic neurons that are anatomically distinct from noradrenergic neurons where DBH resides.

From a clinical point of view, what is needed is a method of identifying prior to the initiation of treatment, those individuals in need of such treatment that are most likely to respond to dopamine agonist therapy in terms of improving symptoms of Type 2 diabetes, pre-diabetes, or Metabolic Syndrome. The ability to identify responders to dopamine agonist therapy, and particularly among Type 2 diabetics, pre-diabetics, and/or Metabolic Syndrome subjects prior to exposure to the therapy itself would greatly increase the benefit-to-risk ratio for such therapy among treated subjects, which is the goal of all medical interventions, treatments, and therapies. Identification of responders would minimize the risk of needless exposure or inappropriate treatment in lieu of other more appropriate treatment strategies among those individuals classified as non-responders to dopamine agonist therapy in whom, on average, no clinical benefit is expected. The present invention is believed to be an answer to the above needs.

BRIEF SUMMARY OF THE INVENTION

In one aspect, the present invention is directed to a method of identifying patients to be treated by dopamine agonist therapy comprising the step of analyzing a plasma or urine sample from said patient for concentrations of norepinephrine (NE), norepinephrine metabolites (NE metabolites), dopamine, dopamine metabolites, serotonin, serotonin metabolites, or fasting triglycerides wherein one or more of: (a) NE metabolites, (b) NE/NE metabolites : dopamine/dopamine metabolites, (c) NE and serotonin, (d) NE/NE metabolites and serotonin, (e) NE and serotonin metabolites, (f) NE/NE metabolites and serotonin metabolites, or (g) NE, is/are greater than about 30% over normal level; or dopamine/dopamine metabolites are less than about 30% below normal; or fasting triglycerides are greater than about 150mg/dl and/or said patient has blood pressure of greater than about 135/85 mm Hg.

In another aspect, the present invention is directed to a method of treating a patient suffering from a metabolic condition, comprising the steps of:
  (a) identifying patients to be treated by dopamine agonist therapy according to the above procedure, and
  (b) administering to the identified patients a pharmaceutically effective regimen of dopamine agonist therapy;
    wherein the metabolic condition is selected from the group consisting of Type 2 diabetes, pre-diabetes, Metabolic Syndrome, obesity, hyperglycemia, glucose intolerance, hyperinsulinemia, insulin resistance, elevated plasma lipid levels, and combinations thereof.

These and other aspects will be described in more details in the following detailed description of the invention.

DETAILED DESCRIPTION OF THE INVENTION

In accordance with the method of the present invention, it has been surprisingly discovered that it is possible to identify patients that are suffering from Type 2 diabetes, pre-diabetes, Metabolic Syndrome, or obesity, and determine if they are good candidates (termed "responders") for dopamine agonist therapy. These responders have a higher likelihood of successful treatment, generally as a percent of the population in the range of 70% or better as compared to 25-35% among a random selection of suffering patients. Identification of patients who will respond well to dopamine agonist therapy prevents inappropriate and/or unnecessary treatment to some individuals.

As indicated above, the present invention is a method of identifying patients to be treated by dopamine agonist therapy comprising the step of analyzing a plasma or urine sample from said patient for concentrations of norepinephrine (NE), norepinephrine metabolites (NE metabolites), dopamine, dopamine metabolites, serotonin, serotonin metabolites, or fasting triglycerides. If one or more of: (a) NE metabolites, (b) NE/NE metabolites:
dopamine/dopamine metabolites, (c) NE and serotonin, (d) NE/NE metabolites and serotonin, (e) NE and serotonin metabolites, (f) NE/NE metabolites and serotonin metabolites, or (g) NE is/are greater than about 30% over normal level; or dopamine/dopamine metabolites are less than about 30% below normal; or fasting triglycerides are greater than about 150 mg/dl and/or said patient has blood pressure of greater than about 135 (Systolic)/85 (Diastolic) mm Hg, the individual is identified as a responder to dopamine agonist therapy.

As a preliminary step, it may be desirable to identify the metabolic disorder of the individual (e.g., Type 2 diabetes, pre-diabetes, Metabolic Syndrome, obesity, hyperglycemia, glucose intolerance, hyperinsulinemia, insulin resistance, elevated plasma lipid levels, etc.) with appropriate clinical measures of plasma glucose, insulin, lipids, glucose tolerance, blood pressure, obesity, and the like. These determinations may be made by analytical methods and tests well known in the art, for example spectrophotometry, radioimmunoassay, and anthropomorphic measurements.

A urine or plasma sample from the patient is analyzed using conventional techniques such as spectrophotometry, high pressure liquid chromatography (HPLC), and the like.

Preferably, the urine or plasma sample is obtained in the morning, after rising from sleep. The analysis should measure the concentrations of the following compounds: norepinephrine (NE), norepinephrine metabolites (NE metabolites), dopamine, dopamine metabolites, serotonin, serotonin metabolites, and/or fasting triglycerides. In one embodiment, the absolute concentration of compounds or combinations of compounds may be used, such as NE metabolites, NE and serotonin, NE/NE metabolites and serotonin, NE/NE metabolites and serotonin metabolites, or NE and serotonin metabolites. In another embodiment, the ratio of two of the concentrations of compounds may be used, such as NE/NE metabolites : dopamine/dopamine metabolites. An indication of a favorable response to dopamine agonist therapy is indicated when one or more of these values are greater than about 30% over normal level.

In another embodiment, an indication of a favorable response to dopamine agonist therapy is indicated when dopamine or dopamine metabolites are less than about 30% below normal.

In another embodiment, an indication of a favorable response to dopamine agonist therapy is indicated when fasting triglycerides are greater than about 150 mg/dl and/or the patient has blood pressure of greater than about 135/85 mm Hg.

Once responders are identified, treatment of their metabolic disorder with a dopamine agonist may begin. Those individuals identified as responders are anticipated to react well to the dopamine agonist therapy.

The dopamine agonist treatment therapy may be administered by any method known in the art, for example administration of bromocriptine or pharmaceutical formulations thereof.

A positive response to dopamine agonist therapy can be identified by simple tests performed on patients undergoing the treatment. In one embodiment, a positive response to the therapy in patients with Type 2 diabetes is indicated by the decline from baseline of HbAlc of at least 0.5 over a 12-24 week treatment period. In another embodiment, a positive response in patients with pre-diabetes is indicated by a fasting glucose level reduced below about 110 mg/dl or the 2-hour OGTT reduced below about 175 mg/dl. In yet another embodiment, patients with Metabolic Syndrome who have a positive response to the dopamine agonist therapy have improvements by at least 3-5% of any three of glucose tolerance, fasting plasma glucose, postprandial plasma glucose, plasma triglyceride, plasma HDL-cholesterol, blood pressure, or obesity.

While the invention has been described in combination with embodiments thereof, it is evident that many alternatives, modifications and variations will be apparent to those skilled in the art in light of the foregoing description. Accordingly, it is intended to embrace all such alternatives, modifications and variations as fall within the spirit and broad scope of the appended claims. All patent applications, patents, and other publications cited herein are incorporated by reference in their entireties.

What is claimed is:

1. A method of identifying patients to be treated by dopamine agonist therapy comprising the steps of:
    analyzing a plasma or urine sample from said patient for concentrations of norepinephrine (NE), norepinephrine metabolites (NE metabolites), dopamine, dopamine metabolites, serotonin, serotonin metabolites, or fasting triglycerides, wherein one or more of:
        a) NE metabolites,
        b) NE or NE metabolites: dopamine or dopamine metabolites,
        c) NE and serotonin,
        d) NE or NE metabolites and serotonin,
        e) NE and serotonin metabolites,
        f) NE or NE metabolites and serotonin metabolites, or
        g) NE,
    is/are greater than about 30% over normal level; or
    dopamine or dopamine metabolites are less than about 30% below normal; or
    said patient is suffering from hypertriglyceridemia and/or hypertension.

2. The method of claim 1, wherein said patient is further suffering from a condition selected from the group consisting of cardiovascular disease, Type 2 diabetes, pre-diabetes, Metabolic Syndrome, obesity, hyperglycemia, glucose intolerance, hyperinsulinemia, insulin resistance, elevated plasma lipid levels, and combinations thereof.

3. A method of treating a patient suffering from a metabolic condition, comprising the steps of:
    (a) identifying patients to be treated by dopamine agonist therapy according to claim 1, and
    (b) administering to said identified patients a pharmaceutically effective regimen of dopamine agonist therapy;
    wherein said metabolic condition is selected from the group consisting of cardiovascular disease, Type 2 diabetes, pre-diabetes, Metabolic Syndrome, obesity, hyperglycemia, glucose intolerance, hyperinsulinemia, insulin resistance, elevated plasma lipid levels, and combinations thereof.

4. The method of claim 2, wherein said pharmaceutically effective regimen of dopamine agonist therapy comprises administration of bromocriptine.

* * * * *